United States Patent [19]

Fitch et al.

[11] 4,145,440

[45] Mar. 20, 1979

[54] LIQUID SUSPENSION OF AN ALUMINUM SALT OF IBUPROFEN

[75] Inventors: Kandy A. Fitch; Englebert L. Rowe, both of Portage Township, Kalamazoo County, Mich.

[73] Assignee: The Upjohn Company, Kalamazoo, Mich.

[21] Appl. No.: 825,572

[22] Filed: Aug. 18, 1977

[51] Int. Cl.$^2$ ............... A61K 47/00; A61K 31/19; A61K 31/28; C07F 5/06
[52] U.S. Cl. ............... 424/287; 260/448 R; 424/315; 424/317; 424/362
[58] Field of Search ............... 424/287, 315, 317, 361, 424/362; 260/515 A, 448 R

[56] References Cited

U.S. PATENT DOCUMENTS

| | | | |
|---|---|---|---|
| 3,228,831 | 1/1966 | Nicholson | 424/317 |
| 3,385,886 | 5/1968 | Nicholson | 260/515 A |
| 3,636,200 | 1/1972 | Zentner | 424/362 X |
| 3,865,857 | 2/1975 | Suzuki | 260/448 R |
| 3,976,674 | 8/1976 | Fields | 424/317 |
| 3,985,779 | 10/1976 | Tanaka | 260/448 R |

FOREIGN PATENT DOCUMENTS 811810  9/1974  Belgium ............... 424/287

OTHER PUBLICATIONS

Remington's Pharm. Sci., Mack Pub. Co., Easton, Pa., 15th ed. 1975, pp. 322-327, 1456-1460.

Primary Examiner—Anna P. Fagelson
Attorney, Agent, or Firm—John T. Reynolds

[57] ABSTRACT

Liquid pharmaceutical suspensions of aluminum ibuprofen salts, which are gel resistant, non-caking, have controlled sedimentation properties and which are easily re-suspended by shaking the suspension bottle, can be obtained by dispersing aluminum ibuprofen salts in a sorbitol/glycerin/water mixture containing controlled maximum amounts of pharmaceutically acceptable suspending agents and water soluble surface active agents.

9 Claims, No Drawings

LIQUID SUSPENSION OF AN ALUMINUM SALT OF IBUPROFEN

INTRODUCTION

This invention relates to pharmaceutical compositions of aluminum salts of ibuprofen. More particularly, this invention provides new gel resistant, non-caking, liquid pharmaceutical suspensions of aluminum ibuprofen which are easily shakable to a homogeneous consistency for uniform dosing.

BACKGROUND OF THE INVENTION

Nicholson et al. U.S. Pat. No. 3,385,886 claims 2-(4-isobutylphenyl)propionic acid (ibuprofen) as a compound per se. Nicholson et al. U.S. Pat. No. 3,228,831 discloses the use of ibuprofen as a drug to alleviate the symptoms of inflammation in animals. Since its introduction as a commercially available drug for human use, there has been much medical literature about ibuprofen. Ibuprofen is sold as coated tablets because ibuprofen per se has a bitter, sharply disagreeable taste. The distinct acid taste of ibuprofen is masked by the coating which permits oral administration without giving the bitter or burning acid taste of the free acid. Continued research for better modes in which to administer ibuprofen continues for the purposes of eliminating or reducing the cost of and the need for coatings presently used to overcome as much as possible the disagreeable acid taste of ibuprofen.

It has been found that the usual sodium, calcium and magnesium salts of this acid also contain a discernible disagreeable taste.

Recently, it was discovered that aluminum salts of ibuprofen provide an essentially tasteless, effective pharmaceutical form of ibuprofen which salts can be manufactured economically and compounded into pharmaceutical liquid suspension and solid formulations for administration in unit dosage forms. The use of these aluminum ibuprofen salts obviates the coating operation previously required with ibuprofen per se. These aluminum salts are disclosed and claimed in Sinkula U.S. Application Ser. No. 640,431, filed Dec. 15, 1975.

Aluminum ibuprofen salts are not soluble in water or other usual pharmaceutical excipients to any substantial extent and they are difficult to wet and disperse uniformly in liquid mixtures. These salts would normally be compounded into any of various solid dosage forms. However, pharmaceutical liquid suspension forms of these salts would be preferred when the patients are to be small children or elderly persons because these patient populations often have difficulty swallowing tablets, capsules or other solid forms of drugs.

In preparing suspensions of water-insoluble drug compounds such as these aluminum ibuprofen salts, the particular pharmaceutical vehicle or diluent mixture which is best for these salts is not readily predictable from knowledge and experience with other similar drug acid salts. Substitution of an aluminum salt of one drug acid into a pharmaceutical formulation of another aluminum salt of a drug acid does not often produce an acceptable pharmaceutical composition for the dosage use intended.

To be an acceptable pharmaceutical product the aluminum ibuprofen salt suspension must have a suitable long shelf life, say, 1 to 3 years, the liquid suspension must not gel to any significant extent, the solids in the liquid suspension must not settle to form a hard non-uniformly dispersible cake, and the amount of sedimentation of the solids in the suspension must be controlled to within a range of from about 60 to 95 percent of the suspension liquid volume, preferably to about 70 to 85 percent of the suspension liquid volume. There is a need in the pharmaceutical art for a pharmaceutical formulation of aluminum ibuprofen salts which will provide the ibuprofen drug in a form which will be more acceptable to the various types of patients, the pharmacists and manufacturers of this drug.

OBJECTS OF THE INVENTION

It is an object of this invention to provide new homogeneously dispersible liquid pharmaceutical suspension compositions of aluminum ibuprofen salts.

It is another object of this invention to provide new gel resistant, non-caking, controlled sedimentation liquid pharmaceutical suspension compositions of aluminum ibuprofen salts, which suspensions are easily shakable to a homogeneous consistency for uniform dosing over an extended shelf life.

Other objects, aspects and advantages of the invention will become apparent from the remaining specification and the claims which follow.

SUMMARY OF THE INVENTION

Briefly, according to this invention, we have discovered that liquid, pharmaceutical suspensions satisfying the above objects can be obtained by suspending the aluminum ibuprofen salts in liquid pharmaceutical vehicles containing maximum, controlled amounts of microcrystalline cellulose, sodium carboxymethylcellulose, or magnesium aluminum silicate suspending agents, or mixtures thereof and pharmaceutically acceptable water soluble surface active agents in a sorbitol/glycerin/water mixture. These ingredients can be compounded to form pleasant tasting aqueous suspensions which are pharmaceutically elegant while also having the desired excellent physical and chemical stability properties desired for aluminum salt forms of ibuprofen.

DETAILED DESCRIPTION OF THE INVENTION

More particularly, this invention provides pharmaceutical liquid suspension compositions comprising, for each 100 ml. of suspension,
   (a) from about 4 to about 17 grams of an aluminum salt of ibuprofen,
   (b) from about 0.25 to about 2.25 grams of a pharmaceutically acceptable suspending agent having an average particle size below about 50 microns.
   (c) from about 0.4 to about 0.8 grams of a non-toxic, pharmaceutically acceptable essentially water soluble surface active agent,
   (d) from about 10 to 30 milliliters of 70 percent U.S.P. sorbitol solution;
   (e) from about 5 to about 20 milliliters of glycerin U.S.P., and
   (f) sufficient water to bring the liquid volume to 100 ml. of total liquid suspension.

Preferred compositions of this invention are those described above wherein the suspending agent (b) is selected from the group consisting of
   (1) a mixture of about 0.9 to about 1.4 weight percent of microcrystalline cellulose and about 0.1 to about 1 weight percent of sodium carboxymethylcellulose, (2) about 0.25 to about 0.8 weight percent of a magnesium aluminum silicate powder, and (3) mixtures of (1) and (2), that is, so that the total weight of the suspending agent (1) and (2) mixture is not more than about 2.25 weight percent of the total liquid suspension.

The suspension can also, optionally contain up to about 10 ml. of 95 percent ethanol, for each 100 ml. of suspension, before the water is added to make the total volume of suspension. The ethanol aids the wetting of the solid ingredients in the suspension.

The composition may also, optionally have added thereto up to about 0.4 ml. of sorbic acid, N.F., for each 100 ml. of suspension, or other equivalent substance to inhibit the presence, growth and action of mold or yeast.

The composition may also, optionally include sweetening agents such as up to about 1 g. of sodium saccharin powder, 109 percent N.F. or other equivalent sweeteners, such as finely divided mono- and disaccharides, e.g., sucrose, fructose, glucose and non-carbohydrate sweeteners known in the art.

Examples of flavoring agents which can be included in amounts up to about 1 gram per 100 ml. of suspension, include Orange-Lemon Flavor PFC 8432, and other pharmaceutically acceptable flavors, such as Cherry Flavor, Peppermint oil, double distilled, eucalyptol, anethol, methyl salicylate, oil cassia or cinnamic aldehyde, and the like.

A preferred composition according to this invention is one which comprises, for each 100 ml. of liquid suspension,
(a) from about 4.4 to about 14 grams of an aluminum ibuprofen salt, which will provide about 4 to about 12 grams of ibuprofen equivalent in the suspension composition,
(b) about 1.7 grams of a suspending agent mixture consisting of about 0.9 to about 1.2 grams of microcrystalline cellulose and about 0.1 to about 0.9 grams of sodium carboxymethylcellulose;
(c) about 0.4 to about 0.8 grams of Polysorbate 80 U.S.P.;
(d) about 15 to 25 milliliters of 70 percent sorbitol U.S.P. solution;
(e) about 5 to about 15 milliliters of glycerin U.S.P.,
(f) up to about 0.3 grams of sorbic acid N.F.,
(g) up to about 0.5 grams sodium saccharin powder 109 percent N.F., and
sufficient water to make 100 ml. of the liquid suspension.

The aluminum ibuprofen salt in the suspension is a salt of the formula

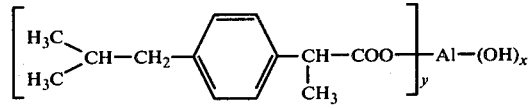

where x is 0 to 2, y is 1 to 3, so that the sum of x and y is equal to 3. This formula is intended to include mixtures of mono-ibuprofen aluminum salt, di-ibuprofen aluminum salt and tri-ibuprofen-aluminum salt molecules so that in a typical aluminum salt sample the average ratio of ibuprofen moiety to aluminum atom in the sample can range between, say 0.9 and 2.9. The preferred aluminum ibuprofen salts for use in these compositions are those having an average ratio of between about 1 and 2 ibuprofen acid equivalents per aluminum atom. We are developing an aluminum ibuprofen suspension of this invention using an aluminum ibuprofen salt which contains an average of about two ibuprofen moieties per atom of aluminum, although aluminum ibuprofen salts containing down to about 1 equivalent of ibuprofen per aluminum atom work very well in these suspensions. Aluminum ibuprofen salts containing close to the maximum ratio of three ibuprofen equivalents per aluminum atom can be used but they are not preferred because they are difficult to purify from adhering ibuprofen, which, as indicated above, contributes to a disagreeable taste.

These new suspensions are designed and prepared so as to contain per a 5 ml. dose between about 200 mg. and about 600 mg. of ibuprofen equivalent in the form of the aluminum ibuprofen salt. The weight percent of the aluminum ibuprofen salt is used which corresponds to the selected concentration. For example, for a pediatric suspension containing, say, about 200 mg. of ibuprofen equivalent per 5 ml. dose, the weight of an aluminum di-ibuprofen salt per 100 ml. of suspension being prepared would be about 4.4 grams. For a normal adult size 400 mg. dose of ibuprofen equivalent the weight content of the same aluminum di-ibuprofen salt would be about 8.8 and for a stronger 600 mg. dose of ibuprofen equivalent the dosage of such di-ibuprofen aluminum salt would be about 13.2 grams of this aluminum di-ibuprofen salt per 100 ml. of suspension.

A preferred composition in accordance with this invention would comprise, for each 100 ml. of suspension, which is to contain about 400 mg. of ibuprofen equivalent per 5 ml. as its aluminum salt,
(a) about 8.8 grams of the aluminum di-ibuprofen salt;
(b) from about 1.0 to about 1.25 grams of pharmaceutical grade microcrystalline cellulose and about 0.1 to about 1.0 grams of sodium carboxymethylcellulose, or about 0.25 to about 0.8 grams of Veegum ® F, as suspending agent;
(c) about 0.4 to about 0.8 grams of a polyoxyethylene sorbitan mono $C_{16}$ to $C_{20}$-alkanoate surfactant containing an average of about 18 to 22 oxy ethylene groups per surfactant molecule (e.g., Polysorbate 60 or 80 U.S.P.);
(d) about 10 to 30 milliliters of a 70 percent sorbitol U.S.P. solution;
(e) about 5 to 15 milliliters of glycerin U.S.P.;
(f) up to about 0.4 milliliters of sorbic acid N.F.;
(g) up to about 1.0 gram of sodium saccharin powder 109 percent N.F., and sufficient water to bring the liquid volume to 100 ml. of total liquid suspension.

The aluminum ibuprofen salts can be prepared by suspending or dispersing the ibuprofen in water, adding base, e.g., sodium hydroxide, to the mixture to effect dissolution of the ibuprofen acid in the mixture. Then this ibuprofen-base solution can be added to or otherwise blended with a solution of a pharmaceutical grade aluminum acid salt, e.g., with a solution of aluminum nitrate, chloride or sulfate. Aluminum nitrate is preferred. Precipitation of the respective aluminum salt commences almost immediately. After the selected proportion of ibuprofen or dissolved ibuprofen salt thereof has been mixed with the aluminum salt solution, the mixture can be stirred or otherwise agitated to insure complete reaction. The solid aluminum ibuprofen salt can be separated from its reaction mixture by filtration, washed with water, dried in vacuo at 50° to 60° C. to constant weight. Thereafter the aluminum ibuprofen salt is ready for compounding into the suspension compositions of this invention. The aluminum ibuprofen salt can also be prepared by reacting the ibuprofen with an aluminum alkoxide at room temperature or by heating the mixture in an aromatic hydrocarbon solvent such as benzene or toluene, or a $C_1$ to $C_3$-alkanol such as methanol, ethanol or n- or isopropanol, as described in Japanese patent publication No. J5-1067-717 (Derwent No. 56971X30). Detailed examples of preferred methods for preparing these aluminum ibuprofen salts are set forth below.

The suspending agents useful in the suspensions of this invention include Acacia U.S.P., Bentonite U.S.P., Carbomer N.F., Carboxymethylcellulose sodium U.S.P., Polyvinyl alcohol U.S.P., Povidone U.S.P., Tragacanth U.S.P., Xanthan Gum NF, Microcrystalline Cellulose N.F., and the like, which for the most part are powders, having average particle sizes below about 50 microns.

Examples of preferred suspending agents for use in the pharmaceutical suspensions of this invention include:

(1) Avicel ® RC-591, which is a commercially available microcrystalline cellulose marketed by FMC Corporation, Avicel Department, Marcus Hook, Pa., 19601, and which is said to be a colloidal form of about 89 percent microcrystalline cellulose gel blended with about 11 percent sodium carboxymethylcellulose and dried, and which product is easily dispersed in water. It is insoluble in water, organic solvents and dilute acids. It is partially soluble in dilute alkali. Its chemical and physical specifications are: loss on drying: less than 6 percent at time of shipment; heavy metals: less than 10 parts per million; viscosity of a 1.2 percent solution, 65 ± 25 centipoise; pH (1 percent solids aqueous suspension): 6 to 9; Assay: sodium carboxymethylcellulose content 11.0 ± 1 percent; particle size: less than 0.1 percent retained on 60 mesh screen, less than 20 percent retained on a 325 mesh screen. Average particle size is about 28 microns. Its bulk density is about 37 lbs./ft.$^3$ loose pack and about 52 lbs./ft.$^3$ tight pack. Its specific gravity is 1.55, ash content about 2 percent, pH of a 2 percent dispersion in water is 6 to 8. Other similar pharmaceutical grade microcrystallinecellulose products can be used.

(2) Veegum ® F which is a microfine powdered magnesium aluminum silicate manufactured and sold by R. T. Vanderbilt Company, Inc., Specialties Department, 230 Park Avenue, New York, N.Y., 10017. This powdered suspending agent is said to be an inorganic, complex, colloidal magnesium aluminum silicate having an average chemical analyses, expressed as oxides as follows:

| | | |
|---|---|---|
| Silicon dioxide | 61.1 | Percent |
| Magnesium oxide | 13.7 | Percent |
| Aluminum oxide | 9.3 | Percent |
| Titanium oxide | 0.1 | Percent |
| Ferric oxide | 0.9 | Percent |
| Calcium oxide | 2.7 | Percent |
| Sodium oxide | 2.9 | Percent |
| Potassium oxide | 0.3 | Percent |
| Carbon dioxide | 1.8 | Percent |
| Water of combination | 7.2 | Percent | which has a particle size which passes a 325 mesh screen.

We have found that for pharmaceutical liquid suspensions of aluminum ibuprofen meeting the above criteria, it is important to control the amount of suspending agent ranging from at least about 0.25 weight percent to about 2.25 percent by weight, preferably below about 2 percent, the particular amounts depending upon the choice of suspending agent. If the weight amounts of suspending agents are below the lower limits stated the material does not suspend properly and as a result, the solid components of the suspension precipitate to form a cake which is difficult to disperse; if the amounts of the suspending agents are much above the 2.25 weight percent range, the suspension becomes excessively thick and does not flow.

The wetting agents or surface active agents used in the suspension of this invention must be pharmaceutically acceptable, that is, non-toxic, and essentially water soluble in the amounts used and be effective to keep the solid form ingredients soluble or compatible with the suspension formulation. The wetting agent or surface active agent can be a non-ionic, anionic or cationic chemical compound or composition which should perform its function at a concentration of no more than about 0.8 weight percent, based on about 100 ml. of liquid suspension. Examples of preferred water soluble wetting agents or surfactants for these aluminum ibuprofen suspensions include Polysorbate 80 (polyoxyethylene(20)sorbitan monooleate), Polysorbate 60 (polyoxyethylene(20)sorbitan monostearate), Myrj 52 (polyoxyethylenestearate U.S.P.), glycerol monostearate, glycerol monooleate, glycerol monoricinoleate, Plurnic F-68 (a polyoxyethylene-polyoxypropylene copolymer containing about 80 percent polyoxyethylene units and a polyoxypropylene moiety whose molecular weight is about 1750) as non-ionic surfactants, sodium lauryl sulfate as an anionic surfactant, and myristyl α-picolinium chloride as a cationic surfactant.

This invention is further illustrated and exemplified by the following detailed preparations and examples, but they are not intended as limiting the scope of the invention.

PREPARATIONS

Aluminum Salt of Ibuprofen (2:1)

Ibuprofen (100 gm., 0.487 mole) is suspended in 300 ml. of water. To this suspension is added 500 ml. of 1N NaOH (0.500 mole) with good stirring. Dissolve 90.8 gm. (0.242 mole) of $Al(NO_3)_3.9H_2O$ in 300 ml. of water and simultaneously add the solution of sodium ibuprofen to 200 ml. of $NaHCO_3$ (20.362 gm., 0.242 mole). Precipitation occurs immediately. Stir for one hour, filter the solids, and wash with water. Dry in vacuo at 50° C., melting point 240° +C.

Analyses: Theory (1%): C, 68.70; H, 7.76; Al, 5.94. Found: C, 67.22; H, 7.78; Al, 7.88.

Aluminum Salt of Ibuprofen (1:1)

Ibuprofen (20.63 gm., 0.1 mole) is suspended in 20 ml. of water and 100 ml. of 1N NaOH added. In 150 ml. of water is dissolved 37.5 gm. (0.1 mole) of $Al(NO_3)_3.9H_2O$. The solutions of sodium ibuprofen and $Al(NO_3)_3$ are slowly added simultaneously to 450 ml. of $NaHCO_3$ solution (16.8 gm., 0.2 mole) with stirring. Precipitation commences immediately. Addition takes approximately 10 minutes. The resulting precipitate is stirred for one hour and filtered. The solids are dried in vacuo at 50° C.

Analyses: Theory (1%): C, 58.64; H, 7.19; Al, 10.13.
Found: C, 58.06; H, 7.12; Al, 11.43
KF water — 5.39%
Melting point 240° +C.

Aluminum Salt of Ibuprofen (3:1)

Ibuprofen (150 gm., 0.727 mole) is suspended in 1 liter of water. Add 750 ml. of 1N NaOH (0.727 mole) to the suspension and stir. Slowly add a solution of 90.93 gm. (0.727 mole) of $Al(NO_3).9H_2O$ with good stirring until precipitation is complete. Stir for an additional hour and filter. Dry solids in vacuo at 50° C.

Analyses: Theory (%): C, 72.87; H, 8.00; Al, 4.20.
Found: C, 71.50; H, 8.20; Al, 4.96.
KF water — 3.53%

The highest quality lots of aluminum di-ibuprofen (2:1 salt) were manufactured by the following procedure:

Aluminum Salt of Ibuprofen (2:1)

Ibuprofen (206 g., 1 mole) is dissolved in 800 ml. absolute ethanol and 39.5 g. (0.9875 mole) sodium hydroxide added. The solution is stirred for 1.5 hours and filtered. A solution of 187.5 g. (0.5 mole) of aluminum nitrate.nonahydrate $(Al(NO_3)_3.9H_2O)$ in 400 ml. of absolute ethanol is added dropwise to the ibuprofen solution while stirring rapidly. After addition of the aluminum nitrate is complete, stir two more hours and filter under nitrogen. The clear filtrate is treated with 200 ml. of carbon dioxide-free distilled water and stirred. The mixture is filtered and the filtrate poured into 2000 ml. of rapidly stirring carbon dioxide-free water. Stirring is continued for 3 hours, then the mixture is filtered on a coarse sintered glass filter and the precipitate is washed with one liter of water. The wet solids are homogenized in a high speed blender with 800 ml. of distilled water for 1 minute, then filtered again and washed with 6 one-liter volumes of water followed by 4 one-liter washes using glass-distilled acetonitrile. The compound is dried over phosphorus pentoxide $(P_2O_5)$ in a vacuum dessicator for 7 days, then broken up in a high speed blender and further dried under high vacuum (with $P_2O_5$).

Analyses: Theory (%): C, 68.70; H, 7.76; Al, 5.93.
Found: C, 68.84; H, 7.53; Al, 6.36.
KF water — 1.42%

EXAMPLE 1

Aluminum mono-ibuprofen suspension using Veegum ® suspending agent and ethanol

A. Syrup Vehicle

| Ingredients | for 100 ml. syrup | |
|---|---|---|
| Sorbic Acid NF | 0.2 | g. |
| Polysorbate 80 USP | 0.5 | g. |
| Sodium Saccharin Po. 109% NF | 0.5 | g. |
| Sodium Hydroxide 30% | 0.025 | ml. |
| Glycerin USP | 10.0 | ml. |
| Sorbitol Solution 70% USP | 20.0 | ml. |
| Orange-Lemon Flavor PFC 8432 | 1.0 | ml. |
| 95% Ethanol | 5.0 | ml. |
| Deionized water to make | 100.0 | ml. |

Directions

Heat 50% of the total water on a steam bath to 60° C. Add sorbic acid and sodium hydroxide and stir until dissolved. Cool to 30° C. and add remainder of ingredients. Mix well and add water to bring to volume. Clear syrup results.

B. Veegum ®Dispersion

| Ingredients | for 100 ml. dispersion | |
|---|---|---|
| Veegum ®F (Colloidal Magnesium Aluminum Silicate) | 5.0 | g. |
| Deionized Water to make | 100.0 | ml. |

Heat 90% water on steam bath to 70° C. and stir in Veegum ® F. When well dispersed, cool and bring to indicated volume with water.

C. Suspension

| Ingredients | For 100 ml. Suspension | | |
|---|---|---|---|
| Veegum F ®(Colloidal Magnesium Aluminum Silicate) Dispersion, as above | 5.0 | ml. | (0.25 g. Veegum) |
| 50% Ethanol in Water Solution | 20.0 | ml. | |
| Aluminum Mono-ibuprofen $[Al(OH)_2M]$* | 10.32 | g. | |
| Syrup vehicle, as above, to make | 100.0 | ml. | |

*M denotes ibuprofen acid equivalent

Place aluminum mono-ibuprofen $[Al(OH_2)M]$ in mortar. Add 50% ethanol solution and triturate until a smooth paste is formed. Add syrup vehicle and stir until a suspension is formed. Add Veegum F ® dispersion and stir for at least one hour.

The 10.32 g. of aluminum mono-ibuprofen salt amount is selected to provide about 8 g. of ibuprofen equivalent per 100 ml. of suspension. This amount when administered by teaspoon in a 5 ml. quantity will provide about 400 mg. of ibuprofen equivalent in that 5 ml. dose.

Observations After Several Months

80% sedimentation, resuspends easily, no caking. When Veegum ® suspending agent is replaced by equal amounts of methylcellulose, hydroxypropylmethylcellulose, or sodium carboxymethylcellulose, the suspension cakes badly and redispersion is very difficult.

EXAMPLE 2

Aluminum di-ibuprofen suspension using Avicel ® as suspending agent, no ethanol, heat and Polysorbate 80 for wetting

| Ingredients | Quantity | |
|---|---|---|
| Avicel ®RC-591 (89% microstalline cellulose)(11% sodium carboxymethylcellulose) | 1.5 | g. |
| Sorbic Acid NF | 0.2 | g. |
| Polysorbate 80 USP | 0.5 | g. |
| Sodium Saccharin Po. 109% | 0.5 | g. |
| Glycerin USP | 10.0 | ml. |
| Sorbitol Solution 70% USP | 20.0 | ml. |
| Aluminum Di-ibuprofen $[Al(OH)M_2]$ | 8.8 | g. |
| Deionized Water to make | 100.0 | ml. |

Disperse Avicel ® RC-591 in 40% of deionized water by stirring at high speed for 0.5 hour. Add sorbic acid, Polysorbate 80, saccharin, glycerin and sorbitol. Mix well. Heat mixture to 65° ± 10° C. and add aluminum di-ibuprofen $[Al(OH)M_2]$ slowly with moderate agitation. Cool to 30° C. and make to volume with deionized water. Homogenize and stir slowly to remove excess air.

Homogeneous, thioxotropic suspension results, gels slightly, but shakes easily to a uniform pourable suspension.

EXAMPLE 3

Aluminum di-ibuprofen suspension using Avicel ® as suspending agent and additional sodium carboxymethylcellulose Preferred Formula

| Ingredients | Quantity | |
|---|---|---|
| Avicel[200] RC-591 (89% microcrystalline cellulose)(11% sodium carboxymethylcellulose) | 1.1 | g. |
| Sodium carboxymethylcellulose | 0.6 | g. |
| Sorbic Acid NF | 0.2 | g. |
| Polysorbate 80 USP | 0.5 | g. |
| Sodium Saccharin Po. 109% NF | 0.5 | g. |
| Glycerin USP | 10.0 | ml. |
| Sorbitol Solution 70% USP | 20.0 | ml. |
| Aluminum di-ibuprofen [Al(OH)M$_2$] | 8.8 | g. |
| Deionized Water to make | 100.0 | ml. |

Disperse Avicel ® RC-591 suspending agent in 40% deionized water with propeller mixer at high speed for 0.5 hour. Wet additional sodium carboxymethylcellulose with glycerin and add to the Avicel dispersion. Add sorbic acid, Polysorbate 80, saccharin and sorbitol and mix well. Heat mixture to 65° C. ± 10° C. and add aluminum di-ibuprofen slowly with moderate agitation. Cool to 30° C. and make to volume with deionized water. Homogenize and stir slowly to remove excess air.

Observations After Several Months

Homogeneous white suspension, coats bottle, forms a smooth pourable suspension with gentle shaking.

Preparation of Aluminum ibuprofen in Prior Art Vehicle

Aluminum-mono-ibuprofen suspension made according to Belgian Pat. No. 811,810.

| Ingredients | Quantity | |
|---|---|---|
| Deionized water | 40.0 | ml. |
| Avicel ®RC-591 (89% microsrystalline cellulose) (11% sodium carboxymethylcellulose) | 2.5 | g. |
| Methyl Paraben | 0.008 | g. |
| Sucrose | 40.0 | g. |
| Aluminum Mono-ibuprofen [Al(OH)$_2$M] | 10.32 | g. |
| Deionized water to make | 100.0 | ml. |

Heat 40% deionized water in a suitable vessel to 60° C. Add methyl paraben and stir at a moderate rate until all dissolved. Add Avicel and maintain temperature at 30° C. for 0.5 hour while stirring. Cool and add sucrose and aluminum-mono-ibuprofen [Al(OH)$_2$M]. Bring up to volume with deionized water, homogenize and stir gently to remove excess air.

A very thick, non-pourable, unsatisfactory suspension results. Thus the prior art composition for another similar anti-inflammatory product was unsatisfactory for aluminum ibuprofen.

EXAMPLE 4

Aluminum-mono-ibuprofen suspension using Veegum ® Syrup Vehicle

| Ingredients | Quantity | |
|---|---|---|
| Sorbic Acid NF | 0.2 | g. |
| Polysorbate 80 USP | 0.5 | g. |
| Sodium Saccharin Po. 109% NF | 0.5 | g. |
| Sodium Hydroxide 30% | 0.025 | g. |
| Glycerin USP | 10.0 | ml. |
| Sorbitol Solution 70% USP | 20.0 | ml. |
| Orange-Lemon Flavor PFC 8432 | 1.0 | ml. |
| 95% Ethanol | 5.0 | ml. |
| Deionized water to make | 100.0 | ml. |

Heat 50% water on a steam bath to 60° C. Add sorbic acid and sodium hydroxide and stir until dissolved. Cool to 30° C. and add remainder of ingredients. Mix well and bring up to volume with water. Clear syrup results.

| Veegum F ®Suspension | | |
|---|---|---|
| Ingredients | Quantity | |
| Veegum F ®(colloidal magnesium aluminum silicate) | 5.0 | g. |
| Deionized water to make | 100.0 | ml. |

Heat 90 ml. water on steam bath to 70° C. and stir in Veegum F ®. When all dispersed, cool and make to volume with water.

| Suspension | | | |
|---|---|---|---|
| Ingredients | Quantity | | |
| Aluminum mono-ibuprofen [Al(OH)$_2$M] | 10.32 | g. | |
| Veegum F ®suspension 5% (colloidal magnesium aluminum silicate) | 10.0 | ml. | (0.5% Veegum) |
| Syrup vehicle to make | 100.0 | ml. | |

Heat syrup to approximately 50° C. Add Veegum and stir at moderate rate for 0.5 hour. Maintain temperature and add aluminum mono-ibuprofen [Al(OH)$_2$M] slowly. Cool to 30° C. and bring up to volume with deionized water containing 5% ethanol to make up loss due to evaporation. Homogenize and stir slowly to remove excess air.

Observations After Several Months

74% sedimentation, clear supernate, no cake, redisperses easily.

EXAMPLE 5

Aluminum di-ibuprofen suspension using Veegum ®

| Ingredients | Quantity | |
|---|---|---|
| Veegum F ® (colloidal magnesium aluminum silicate) | 0.5 | g. |
| Sorbic Acid NF | 0.2 | g. |
| Polysorbate 80 USP | 0.8 | g. |
| Sodium Saccharin Po. 109% NF | 0.5 | g. |
| Glycerin UPS | 10.0 | ml. |
| Sorbitol Solution USP 70% | 20.0 | ml. |
| Aluminum di-ibuprofen [Al(OH)$_2$M] | 8.8 | g. |
| Deionized water to make | 100.0 | ml. |

Heat 60% water in steam bath to 70° C. Add Veegum F ® and stir 0.5 hour at moderate speed to hydrate. Remove from heat and add sorbic acid, Polysorabate 80, saccharin, glycerin and sorbitol. When cooled to 25°

C., add aluminum di-ibuprofen [Al(OH)$_2$M] slowly. Make to volume with deionized water, homogenize and stir gently to remove excess air.

Observations Serveral Months Later

76% sedimentation, no cake, cloudy supernate, redisperses easily.

All of the above examples except for the Preparation in the Vehicle of Another Aluminum Salt (following Belgian Pat. No. 811,810) are good suspensions suitable for administration to humans. They have a pleasant taste and mouthfeel. The suspensions do not cake even after months of standing. The sedimentation volume and resuspendability are excellent.

We claim:

1. A pharmaceutical liquid suspension composition comprising, for each 100 ml. of suspension,
   (a) from about 4 to about 17 grams of an aluminum salt of ibuprofen,
   (b) from about 0.25 to about 2.25 grams of a pharmaceutically acceptable suspending agent having an average particle size below about 50 microns,
   (c) from about 0.4 to about 0.8 grams of a pharmaceutically acceptable, essentially water soluble surface active agent,
   (d) from about 10 to about 30 milliliters of 70% USP sorbitol solution,
   (e) from about 5 to about 20 milliliters of glycerin USP, and
   (f) water sufficient in amount to bring the liquid volume to 100 ml. of total liquid suspension.

2. A composition according to claim 1 wherein the suspending agent (b) is selected from the group consisting of
   (1) a mixture of about 0.9 to about 1.4 weight percent of microcrystalline cellulose and about 0.1 to about 1 weight percent of sodium carboxymethylcellulose,
   (2) about 0.25 to about 0.8 weight percent of a magnesium aluminum silicate powder, and
   (3) mixtures of (1) and (2), so that the total weight of the suspending agent (1) and (2) mixture is not more than about 2.25 percent.

3. A composition according to claim 1 which further includes up to about 10 milliliters of 95% ethanol for each 100 ml. of suspension before the water (f) is added.

4. A composition according to claim 1 which further includes up to about 0.4 milliliters of sorbic acid for each 100 ml. of suspension before the water (f) is added.

5. A composition according to claim 1, which further includes up to about 1 gram of sodium saccharin powder 109% NF, before the water (f) is added.

6. A composition according to claim 1 which further contains one or more flavoring and coloring agents as required, before water (f) is added.

7. A composition according to claim 1 wherein the aluminum ibuprofen salt is one having a ratio of about 2 ibuprofen equivalents per atom of aluminum in the salt.

8. A composition according to claim 1 wherein the aluminum ibuprofen salt is one having a ratio of about 1 ibuprofen equivalent to 1 aluminum atom in the salt.

9. A composition according to claim 2 which comprises for each 100 ml. of suspension,
   (a) from about 4.4 to about 14 grams of an aluminum ibuprofen salt which will provide about 4 to about 12 grams of ibuprofen equivalent in the composition,
   (b) about 1.7 grams of a suspending agent mixture consisting of about 0.9 to about 1.2 grams of microcrystalline cellulose and about 0.1 to about 0.9 grams of sodium carboxymethylcellulose;
   (c) about 0.4 to about 0.8 grams of a polyoxyethylene sorbitan mono C$_{16}$ to C$_{20}$-alkanoate surfactant containing an average of about 18 to 22 oxyethylene groups per surfactant molecule;
   (d) about 15 to 25 milliliters of 70% sorbitol USP solution;
   (e) about 5 to about 15 milliliters of glycerin USP;
   (f) up to about 0.3 grams of sorbic acid N.F.;
   (g) up to about 0.5 grams sodium saccharin powder 109% N.F., and sufficient water to make 100 ml. of the liquid suspension.

* * * * *